(12) United States Patent
Reverso

(10) Patent No.: US 10,947,564 B2
(45) Date of Patent: Mar. 16, 2021

(54) METHOD FOR PRODUCING METHANE FROM CARBON DIOXIDE BY CO-CULTURE

(71) Applicant: BIOREWEAL S.R.L., Tortoreto (IT)

(72) Inventor: Riccardo Reverso, Cremona (IT)

(73) Assignee: BIOREWEAL S.R.L., Tortoreto (IT)

( * ) Notice: Subject to any disclaimer, the term of this patent is extended or adjusted under 35 U.S.C. 154(b) by 151 days.

(21) Appl. No.: 15/770,687

(22) PCT Filed: Nov. 15, 2016

(86) PCT No.: PCT/EP2016/077771
§ 371 (c)(1),
(2) Date: Apr. 24, 2018

(87) PCT Pub. No.: WO2017/085080
PCT Pub. Date: May 26, 2017

(65) Prior Publication Data
US 2019/0055584 A1 Feb. 21, 2019

(30) Foreign Application Priority Data
Nov. 18, 2015 (IT) .................. 102015000073679

(51) Int. Cl.
C12P 39/00 (2006.01)
C12P 5/02 (2006.01)
B01D 53/84 (2006.01)
B01D 53/75 (2006.01)
B01D 53/62 (2006.01)

(52) U.S. Cl.
CPC ............. *C12P 5/023* (2013.01); *B01D 53/84* (2013.01); *C12P 39/00* (2013.01); *B01D 53/62* (2013.01); *B01D 53/75* (2013.01); *B01D 2251/95* (2013.01); *B01D 2257/504* (2013.01); *B01D 2258/02* (2013.01); *B01D 2258/0283* (2013.01); *B01D 2258/05* (2013.01); *Y02A 50/20* (2018.01); *Y02C 20/40* (2020.08); *Y02E 50/30* (2013.01); *Y02P 20/151* (2015.11); *Y02P 20/59* (2015.11)

(58) Field of Classification Search
CPC combination set(s) only.
See application file for complete search history.

(56) References Cited

U.S. PATENT DOCUMENTS

| 2010/0099157 A1 | 4/2010 | Salvetzki |
| 2011/0165667 A1 | 7/2011 | Mets |

FOREIGN PATENT DOCUMENTS

| DE | 102007031688 A1 | 1/2009 | |
| JP | H06169783 A | 6/1994 | |
| JP | 2011234676 A | 11/2011 | |
| JP | 2013192547 A | 9/2013 | |
| WO | 2006108136 A2 | 10/2006 | |
| WO | WO-2006108136 A2 * | 10/2006 | ............. C12R 1/01 |
| WO | 2008099252 A1 | 8/2008 | |
| WO | WO-2008099252 A1 * | 8/2008 | ............. B01D 53/62 |
| WO | 2009040546 A1 | 4/2009 | |

OTHER PUBLICATIONS

International Search Report dated Jan. 26, 2017 re: Application No. PCT/EP2016/077771; pp. 1-4; citing: DE 10 2007 031688 A1, WO 2006/108136 A2 and WO 2008/099252 A1.
Written Opinion dated Jan. 26, 2017 re: Application No. PCT/EP2016/077771; pp. 1-11; citing: DE 10 2007 031688 A1, WO 2006/108136 A2 and WO 2008/099252 A1.
American Type Culture Collection (ATCC) online catalog entries, downloaded from www.atcc.org/products Jul. 24, 2020, for: Chlorella vulgaris Beijerinck (Chlorella kessleri Fott and Navakova) (ATCC No. 11468), Moorella thermoacetica (ATCC No. 39073), Rhodococcus rhodochrous (ATCC No. 21198), and *Rubrivivax* sp. (ATCC No. 55304) (12 pages total).
American Type Culture Collection (ATCC) online catalog entries, downloaded from www.atcc.org/products Jun. 22-Jun. 30, 2020, for: Methanothermobacter thermoautotrophicus (ATCC No. 29096), Methanococcus deltae (ATCC No. 35294), Methanococcus vannielii (ATCC No. 35089), Methanococcoides methylutens (ATCC No. 33938), Methanococcus maripaludis (ATCC No. 43000), Methanosarcina barkeri Schnellen (ATCC No. 43569), Methanospirillum hungatei (ATCC No. 27890), Methylococcus capsulatus (ATCC No. 33009) (21 pages).
American Type Culture Collection (ATCC) online catalog entries, downloaded from www.atcc.org/products Jun. 30, 2020, for: Methanosarcina mazei (Barker) Mah and Kuhn (ATCC No. BAA-159), Methanococcus aeolicus (ATCC No. BAA-1280), Anaerobaculum mobile (ATCC No. 43122), Lactobacillus helveticus (ATCC No. 55163), *Chlorella vugaris* var. *viridis* (ATCC No. 16487), *Chlorella* sp. (ATCC No. 30582), Euglena gracilis (ATCC No. 12716), *Euglena gracilis* var. *bacillaris* (ATCC No. 10616), *Euglena gracilis* var. *saccharophila* (ATCC No. 12893) (18 pages).
American Type Culture Collection (ATCC) online catalog entries, downloaded from www.atcc.org/products Jun. 30-Jul. 10, 2020, for: Scenedesmus obliquus (ATCC No. 11477), *Anabaena* sp. (ATCC No. 27899), Rhodobacter sphaeroides (ATCC No. 49419), Bacillus coagulans (ATCC No. 10545), Acetoanaerobium noterae (ATCC No. 35199), Rhodovulum sulfidophilum (ATCC No. 35886), and Bacillus smithii (ATCC No. 55404) (14 pages).
Methanocaldococcus jannaschii, DSM 2661 (ATCC 43067), Leibniz Institute DSMZ—German Collection of Microorganisms and Cell Cultures GmbH, online catalog entry downloaded Jul. 24, 2020 from https://www.dsmz.de/collection/catalogue/details/culture/DSM-2661(4 pages).

* cited by examiner

*Primary Examiner* — Heidi Reese
(74) *Attorney, Agent, or Firm* — Cantor Colburn LLP

(57) ABSTRACT

A method for producing methane by biological conversion of carbon dioxide is performed using a symbiosis between one or more methane-generating bacteria and: (i) one or more hetero-autotrophic cyanobacteria and/or microalgae, or (ii) one or more sulfobacteria and/or acetobacteria, wherein the hetero-autotrophic cyanobacteria and/or microalgae, or the sulfobacteria and/or acetobacteria, produce the molecular hydrogen required for the conversion of carbon dioxide into methane performed by the methane-generating bacteria.

14 Claims, No Drawings

METHOD FOR PRODUCING METHANE FROM CARBON DIOXIDE BY CO-CULTURE

TECHNICAL FIELD

The present disclosure relates to a method for producing methane starting from carbon dioxide ($CO_2$). The method according to the disclosure therefore allows to absorb and to dispose of gaseous emissions containing carbon dioxide.

BACKGROUND

In recent years, the release into the atmosphere of gaseous emissions, particularly with a high content of carbon dioxide, has become an increasingly urgent problem, strongly felt both by people and by the administrations entrusted with dealing with environmental issues. The atmospheric release of carbon dioxide, which is the main responsible for climate change phenomena at the global level ("greenhouse effect"), is increasing constantly, due to various and very active sources such as heating systems, the exhausts of cars, and thermoelectric power stations. An EEC analysis shows that currently approximately 34.4% of the $CO_2$ released into the atmosphere is produced by thermoelectric power stations and this percentage is destined to increase further in the future. Whereas the quantity of $CO_2$ in the atmosphere remained substantially unchanged for millennia, as far as we know, since 1880 it has been increasing constantly. Moreover, our planet has a reduced capacity to absorb and dispose of carbon dioxide also due to extensive deforestation and to the reduction of zoo- and phytoplankton, organisms that have a capacity to regulate ecological chains.

The method according to the disclosure therefore seeks to reduce emissions of carbon dioxide into the atmosphere, at the same time producing a raw material that is an important energy resource.

The production of methane through biological means, by virtue of the action of methane-generating bacteria, is a process known in the art and is already performed in various plants for the treatment of solid and liquid waste. However, the production of methane by fermentation of materials that have a very complex and uneven composition, such as indeed waste, is always accompanied by parallel fermentations that lower the methane yield, producing unwanted gases such as $CO_2$, $NO_X$, $SO_2$, etc. These gases, in addition to slowing the growth of the methane-generating bacteria themselves, thus reducing the active biomass for the methane generation method, cause the resulting product to be of low quality in terms of energy value and heat value.

SUMMARY

The aim of the present disclosure is therefore to provide a method for producing methane by biological conversion of carbon dioxide or of exhaust gases containing carbon dioxide released by industrial processes, such as combustions and fermentations.

Within this aim, the disclosure provides a method as described above that allows to obtain methane with a high degree of purity, which can be used advantageously to generate electric power and thermal energy.

In particular, the disclosure also provides a method that allows to obtain methane while reducing the content of unwanted gases (in particular $SO_X$ and $NO_X$).

The disclosure further provides a method as described above that allows to obtain methane with a higher yield than the methods known so far.

Moreover, the present disclosure provides a method in which, simultaneously with the elimination of the carbon dioxide and the production of methane, biological material is also obtained which is to be used in the production of humus and humatic fertilizers, which are used in the agricultural field for organic fertilization and in the reclamation of contaminated soils.

The disclosure also provides a method for producing methane by biological conversion of carbon dioxide that is highly reliable and relatively easy to provide and has competitive costs and substantially no process waste.

This aim, as well as these and other advantages that will become better apparent hereinafter, are achieved by providing a method in which the production of methane by biological conversion of carbon dioxide is performed by means of a symbiosis between one or more methane-generating bacteria and: (i) one or more hetero-autotrophic cyanobacteria and/or microalgae, or (ii) one or more sulfobacteria and/or acetobacteria, selected among very specific microorganisms that are detailed hereinafter. Since the production of methane by methane-generating bacteria requires the use of molecular hydrogen, symbiosis with hetero-autotrophic cyanobacteria and/or microalgae, or with sulfobacteria and/or acetobacteria (hydrogen-producing microorganisms) allows to have the needed raw material available constantly and in a practical manner.

The method provides for: (i) the provision of a symbiotic culture, growing the microorganisms cited above until they reach the steady state, bubbling carbon dioxide in the fermentation reactors with a flow that is proportional to the volume of said fermentation reactors, so as to obtain the production of methane; and (ii) the capture and consequent sending to storage of the methane produced in step (i).

DETAILED DESCRIPTION

In the method according to the present disclosure, carbon dioxide ($CO_2$) is used as raw material. Therefore, gaseous emissions rich in carbon dioxide but also comprising other gaseous components must undergo a pretreatment before being subjected to the biological conversion according to the method described herein. The pretreatment, which is necessary in order to separate the carbon dioxide from any other gaseous components and to purify it from the presence of any pollutants, can be performed by using various known technologies for $CO_2$ capture, such as, by way of nonlimiting example, membrane separation, so-called "pressure swing adsorption" and scrubbing with amines.

In the method according to the present disclosure, methane generation ("methanation") is simultaneous with biological conversion (or "metabolization") of the carbon dioxide.

Methanation occurs by virtue of the action of methane-generating bacteria, which use $CO_2$ and produce methane according to the following reaction:

$$4H_2 + CO_2 \rightarrow CH_4 + 2H_2O; \text{ i.e.,}$$

$$4H_2 + HCO_3^- + H^+ \rightarrow CH_4 + 3H_2O$$

The methane-generating bacteria are capable of performing this reaction by coupling the oxidation of molecular hydrogen ($H_2$) with the reduction of $CO_2$ (final acceptor of the electrons) with re-oxidation of the NAD by virtue of the continuous removal of said $H_2$. $CO_2$ absorption by the methane-generating bacteria, however, is limited to use in the methanogenesis reaction according to the reaction cited above, since these microorganisms are unable to utilize carbon dioxide for their cell growth, requiring instead more complex organic substances. Methane-generating bacteria in fact are unable to perform so-called "carbon fixation", since they lack the ribulose-bisphosphate-carboxylase (RuBisCo) enzyme, responsible for the first reaction of the Calvin cycle.

It has been said that methane-generating bacteria require a continuous flow of $H_2$ to be used as a reducing agent. For this purpose, it has been found that the source of $H_2$ advantageously can consist of specific microorganisms capable of synthesizing this gas. Methanation according to the present disclosure is therefore performed by providing a symbiotic culture between particular methane-generating bacteria and particular microorganisms that produce $H_2$. Two categories of microorganisms have been identified which are capable of providing the methane-generating bacteria with the molecular hydrogen required to produce methane, and both therefore can be used validly in the symbiotic culture provided by the method according to the disclosure. Two types of symbiosis have thus been identified:

symbiosis of the first kind: one or more methane-generating bacteria selected from the ones listed in the following Table 1 and one or more hetero-autotrophic cyanobacteria selected from the ones listed in the following Table 2 and/or one or more microalgae selected from the ones listed in the following Table 3;

symbiosis of the second kind: one or more methane-generating bacteria selected from the ones listed in the following Table 1 and one or more sulfobacteria and/or one or more acetobacteria selected from the ones listed in the following Table 4.

TABLE 1

| Methane-generating bacteria | ATCC no. |
| --- | --- |
| Methanothermobacter thermoautotrophicus | 29096 |
| Methanococcus deltae | 35294 |
| Methanococcus vannielii | 35089 |
| Methanococcoides methylutens | 33938 |
| Methanococcus jannaschii | 43067D-43067D-5 |
| Methanococcus maripaludis | 43000 |
| Methanosarcina barkeri Schnellen | 43569 |
| Methanospirillum hungatei | 27890 |
| Methylococcus capsulatus | 33009 |
| Methanobrevibacter arboriphilus | BAA-1958 |
| Methanosarcina mazei (Barker) Mah and Kuhn | BAA-159 |
| Methanococcus aeolicus | BAA-1280 |

TABLE 2

| Hetero-autotrophic cyanobacteria | ATCC no. |
| --- | --- |
| Camorosporium robinae | 16673 |
| Acetomicrobium flavidum | 43122 |
| Cochilliobus cynodontis | 24938 |
| Sporotomaculatum hydroxybenzoicum | 700645 |
| Formivibrio citricus | 42791 |
| Rhodococcus rhodochrous | 21198 |
| Moorella thermoacetica | 49073; 39073 |
| Lactobacillus helveticus | 55163 |

TABLE 3

| Microalgae | ATCC no. |
| --- | --- |
| Chlorella vulgaris Beijerinck | 11468 |
| Chlorella vulgaris | 13482; 30581; 30821; 9765 |

TABLE 3-continued

| Microalgae | ATCC no. |
| --- | --- |
| Chlorella vulgaris var. viridis | 16487 |
| Chlorella pyrenoidosa | 30582 |
| Euglena gracilis | 12716 |
| Euglena gracilis var. bacillaris | 10616 |
| Euglena gracilis var. saccharophila | 12893 |
| Scenedesmus obliquus | 11477 |
| Pleurochloris commutata | 11474 |
| Anabaena sp. | 27899 |

TABLE 4

| Sulfobacteria and acetobacteria | ATCC no. |
| --- | --- |
| Rhodobacter sphaeroides | 49419; 55304 |
| Bacillus coagulans | 10545 |
| Acetoanaerobium noterae | 35199 |
| Rhodovulum sulfidophilum | 35886 |
| Bacillus smithii | 55404 |

Preferably, it is possible to add to the culture broths of the heterotrophic microorganisms (i.e., all of the microorganisms listed in Tables 1, 3 and 4 and only the heterotrophic microorganisms listed in Table 2) a hydrolysate of one or more yeasts selected from the group consisting of *Saccharomyces cerevisiae* (ATCC no. 4024938 or 9896) and *Zygosaccharomyces florentius* (ATCC no. 200584). The hydrolysate of these yeasts in fact contains a series of organic substances that facilitate the growth of heterotrophic microorganisms. As it is well known to the person skilled in the art, the enrichment of the culture broths with yeast hydrolysate generally comprises the steps of: yeast culture (separately from the microorganisms involved in the symbioses), recovery of the organic mass of these yeasts and lysis; addition of the resulting hydrolysate to the culture broths to be enriched.

The methane-generating bacteria, as already said, are unable to employ $CO_2$ as a source of carbon for growth, but require more complex organic compounds. The cyanobacteria and microalgae used in the symbiosis of the first kind, being strictly photoautotrophic microorganisms, use $CO_2$ and $N_2$ as a source of nourishment, thus further contributing to the elimination of carbon dioxide. Symbiosis of the first kind is therefore preferable if the quantities of carbon dioxide to be disposed of are substantial. The sulfobacteria and acetobacteria used in symbiosis of the second kind, instead, despite being capable of fixing nitrogen, are unable to use $CO_2$ a source of carbon for growth and require more complex organic compounds, in a manner similar to methane-generating bacteria.

Taking into account the nutritional requirements of the microorganisms used, it follows that symbiosis of the first kind must be performed in two separate environments, one dedicated to cyanobacteria/microalgae and one dedicated to the methane-generating bacteria; symbiosis of the second kind can instead be performed by culturing the sulfobacteria/acetobacteria and the methane-generating bacteria in the same environment.

Both kinds of symbiosis can be performed by means of multiple symbiotic cultures in series, i.e., consecutive to each other, preferably in fermentation reactors of progressively larger sizes, as explained in detail hereinafter. Whereas the use of a single symbiotic culture maximizes the production of organic mass to the detriment of methane production, the use of multiple symbiotic cultures in series maximizes the production of methane to the detriment of the production of organic mass. By using two or more symbiotic cultures in series, the organic material produced by the microorganisms of the preceding culture is in fact used as a base nutrient for the growth of the microorganisms of the following culture, thus facilitating a higher transformation of the organic load into methane. Although it is possible to provide a variable number of symbioses in series, it is preferable to perform three to five symbioses in series, more preferably five symbioses in series, a condition which offers the best results in terms of methane production.

The characteristics and the conditions used in the symbiosis between methane-generating bacteria and heteroautotrophic cyanobacteria and/or microalgae (symbiosis of the first kind) and in the symbiosis between methane-generating bacteria and sulfobacteria and/or acetobacteria (symbiosis of the second kind) are described in greater detail hereinafter.

1. Symbiosis of the First Kind

In addition to the different nutritional requirements of cyanobacteria and/or microalgae and of methane-generating bacteria explained above, these two categories of microorganisms are incompatible, in terms of culture conditions, also due to the different pH and aerobiosis conditions they require: cyanobacteria and microalgae require a microaerophilic environment, while methane-generating bacteria require a strict anaerobic environment. The two cultures (and accordingly, the respective reactions for the production of hydrogen and the production of methane) must therefore occur in two distinct environments. On the other hand, these distinct environments must be mutually connected, so as to allow the transfer of the hydrogen produced by the cyanobacteria/microalgae into the culture environment of the methane-generating bacteria.

The hydrogen generated during the growth of the cyanobacteria/microalgae is bubbled in the culture broth of the methane-generating bacteria that use it, together with $CO_2$, in the production of methane. As stated, symbiosis of the first kind is particularly advantageous, since in addition to producing methane it employs a considerable quantity of carbon dioxide as a carbon source for the growth of cyanobacteria and microalgae as well as in the methanation reaction.

The biomasses of cyanobacteria and/or microalgae and of the methane-generating bacteria obtained in the method can be used as organic material both for providing new fermentations and for the production of humus.

Symbiosis of the first kind can be provided in one or more batteries; preferably, each battery consists of a certain number of pairs of fermentation reactors (one for the growth of cyanobacteria/microalgae and one for the growth of the methane-generating bacteria) arranged in series and having increasing effective volumes. The number of batteries, the number of pairs of fermentation reactors of each battery and the effective volume of the fermentation reactors can be variable according to the quantities of carbon dioxide to be treated.

Preferably, it is possible to use one or more batteries, each of which consists of three pairs of fermentation reactors. Furthermore, it is preferable for each pair of fermentation reactors of the battery to have an effective volume that is one order of magnitude greater than the effective volume of the preceding pair of fermentation reactors. Moreover, in order to optimize the method, the process fermentation reactors of the one or more methane-generating bacteria and the process fermentation reactor of the one or more cyanobacteria and/or microalgae can have a size ratio, in terms of effective volumes, comprised between $1/20$ and $1/30$. The expression "process fermentation reactor" refers to the fermentation reactor in which the culture is provided or, in the case of multiple fermentation reactors in series, it refers to the last fermentation reactor of the series; for example, in the preferred case of a battery composed of three pairs of fermentation reactors in series, the process fermentation reactors are the ones of the third pair.

In the following, for the sake of simplicity methanation by symbiosis of the first type is described with a single battery consisting of three fermentation reactors for each one of the two symbiont microorganisms (i.e., three pairs of fermentation reactors); if multiple batteries are used, the same procedure is applied identically to each battery.

First of all, the culture broths for the growth of each symbiont are prepared by using a mixer for liquids for each broth, with a volume equal to approximately 60% of the sum of the effective volumes of the entire fermentation battery; the culture broths are prepared according to the selected microorganisms, following the specifications indicated by the ATCC and as it is known to the person skilled in the art. The typical composition of the culture broths for the various microorganisms is given in Annex A.

Then, in an incubator (for example of the Dubnoff or equivalent type), a seeding liquid is prepared for each symbiont, comprising the selected microorganism and the corresponding culture broth, typically by using a seeding flask with an effective volume equal to approximately $1/100$ of the effective volume of each fermentation reactor of the first pair of the battery. For each pair of fermentation reactors, one fermentation reactor is dedicated to the growth of the cyanobacteria/microalgae and one fermentation reactor is dedicated to the growth of the methane-generating bacteria.

Fermentation Reactors for the Growth of Cyanobacteria and/or Microalgae

The first "preparatory fermentation" of the cyanobacteria and/or of the microalgae occurs in one of the fermentation reactors of the first pair of the battery: the seeding liquid containing the cyanobacterium or the microalga (or optionally the seeding liquids, if multiple microorganisms are used) is poured into one of the fermentation reactors of the first pair of the battery, together with additional culture broth, until the entire effective volume of the fermentation reactor is reached. Once seeding has occurred, carbon dioxide is bubbled in the fermentation reactor with a flow that is proportional to the volume of the fermentation reactor. Preferably, this flow can be determined by multiplying the volume of the fermentation reactor by a coefficient the value of which is chosen as a function of the microorganisms that are present in the fermentation reactor and is comprised between 50 and 200 g/l/h (g/l per hour). In order to allow oxygenic nitration (i.e., the fixation of $N_2$ in the presence of oxygen), which is required for the growth of cyanobacteria and microalgae, a mixture of $N_2/O_2$ is also bubbled in the fermentation reactor in a 49/1 ratio. Fermentation continues, appropriately controlling the temperature, the pH and the addition of microelements, as it is known to the person skilled in the art, until the steady state of growth is reached. In the steady state, the fermentation reactor of the first pair of the battery dedicated to the growth of the cyanobacteria and/or microalgae typically contains at least 3.5 billion cells/ml; a time comprised between 30 and 36 hours is usually required in order to reach this concentration.

Once the steady state has been reached, the entire content of the fermentation reactor of the first pair dedicated to the growth of cyanobacteria or microalgae is transferred into a fermentation reactor of the second pair, loaded beforehand with culture broth for a quantity equal to the difference between the effective volume of the fermentation reactor of the second pair and the volume of the fermented broth contained in the fermentation reactor of the first pair, in which the first preparatory fermentation of cyanobacteria and/or microalgae occurred. This operation can be performed for example by using a volumetric pump. The second "preparatory fermentation" takes place in the fermentation reactor of the second pair of the battery: once the transfer has occurred, carbon dioxide is bubbled in the fermentation reactor with a flow that is proportional to the volume of the fermentation reactor. Preferably, this flow can be determined by multiplying the volume of the fermentation reactor by a coefficient the value of which is chosen as a function of the microorganisms that are present in the fermentation reactor and is comprised between 50 and 200 g/l/h (g/l per hour). In order to allow oxygenic nitration, an $N_2/O_2$ mixture in a 49/1 ratio is also bubbled in the fermentation reactor. Fermentation continues, appropriately controlling the temperature, the pH and the addition of microelements, as it is known to the person skilled in the art, until the steady state of growth is reached. In the steady state, the fermentation reactor of the second pair dedicated to the growth of the cyanobacteria and/or microalgae typically contains at least 3.5 billion cells/ml; a time comprised between 10 and 18 hours is usually required in order to reach this concentration.

Once the steady state has been reached, the entire content of the fermentation reactor of the second pair dedicated to the growth of the cyanobacteria and/or microalgae is transferred into a fermentation reactor of the third pair, loaded beforehand with culture broth for a quantity equal to the difference between the effective volume of the fermentation reactor of the third pair and the volume of the fermented broth contained in the fermentation reactor of the second pair in which the second preparatory fermentation of cyanobacteria and/or microalgae occurred. Once transfer has occurred, carbon dioxide is bubbled in the fermentation reactor with a flow that is proportional to the volume of the fermentation reactor. Preferably, this flow can be determined by multiplying the volume of the fermentation reactor by a coefficient the value of which is chosen as a function of the microorganisms that are present in the fermentation reactor and is comprised between 50 and 200 g/l/h (g/l per hour), more preferably between 100 and 200 g/l/h. In order to allow oxygenic nitration, an $N_2/O_2$ mixture in a 49/1 ratio is also bubbled in the fermentation reactor. Fermentation continues, appropriately controlling the temperature, the pH and the addition of microelements, as it is known to the person skilled in the art. "Process fermentation" occurs in the fermentation reactor of the third pair of the battery dedicated to the growth of the cyanobacteria or microalgae; in this fermentation, both the absorption of carbon dioxide and the production of hydrogen, generally produced with a flow comprised between 20 and 40 g/l/h (g/l per hour), are maximized and given continuity; the hydrogen is captured by means of an extractor (or other equivalent system) and sent to a gas storage system, from which it is then introduced by bubbling in the process fermentation reactor of the methane-generating bacteria, i.e., the fermentation reactor of the third pair dedicated to the growth of the methane-generating bacteria.

In order to maximize and give continuity both to the absorption of $CO_2$ and to the production of $H_2$, once the steady state (in which, as stated, the concentration of microorganisms is typically equal to at least 3.5 billion cells/ml) has been reached, it is possible to repeat in the process fermentation reactor a cycle further comprising the steps of:
  unloading approximately ⅓ of the volume of the fermented broth into a centrifuge provided with a decanter;
  loading new culture broth for a volume equal to the unloaded fermented broth;
  restarting the growth of the microorganisms, with bubbling of the carbon dioxide with a flow that is proportional to the volume of the fermentation reactor and of the $N_2/O_2$ mixture in a 49/1 ratio, until the steady state is reached again.

After the beginning of the process fermentation, the fermentation reactors of the first pair and second pair dedicated to the growth of the cyanobacteria and microalgae generally undergo sterilization, so that they can be reused if due to anomalies in the process fermentation, it is necessary to renew the mass of microorganisms.

The fermented broth unloaded into the decanter centrifuge is separated by the latter into a semisolid component and a liquid component. The semisolid component amounts to approximately 25% by weight of the broth and consists of the biomass (i.e., the microorganisms) which, after sterilization, can be used for the production of humus or for the subsequent symbiotic cultures. The liquid component amounts to approximately 75% by weight of the broth: by means of a purification process, it is possible to recover from the liquid component water to be reused for the preparation of the culture broths and to produce sludges, which also can be used to produce humus or for subsequent symbiotic cultures.

Fermentation Reactors for the Growth of Methane-Generating Bacteria

The first "preparatory fermentation" of the methane-generating bacteria occurs in the fermentation reactor of the first pair of the battery that is not used for the growth of cyanobacteria and/or microalgae: the seeding liquid that contains the methane-generating bacterium (or optionally the seeding liquids if multiple microorganisms are used) is poured into the fermentation reactor of the first pair of the battery, together with additional culture broth, until the entire effective volume of the fermentation reactor is reached. Once seeding has occurred, carbon dioxide is bubbled in the first fermentation reactor with a flow that is proportional to the volume of the fermentation reactor. Preferably, this flow can be determined by multiplying the volume of the fermentation reactor by a coefficient the value of which is chosen as a function of the microorganisms that are present in the fermentation reactor and is comprised between 100 and 300 g/l/h (g/l per hour). Fermentation continues, appropriately controlling the temperature, the pH and the addition of nutrients and microelements, as it is known to the person skilled in the art, until the steady state of growth is reached. In the steady state, the fermentation reactor of the first pair of the battery dedicated to the growth of the methane-generating bacteria typically contains at least 3.5 billion cells/ml; a time comprised between 30 and 36 hours is usually required in order to reach this concentration.

Once the steady state has been reached, the entire content of the fermentation reactor of the first pair is transferred into the fermentation reactor of the second pair dedicated to the growth of the methane-generating bacteria, loaded beforehand with culture broth for a quantity equal to the difference between the effective volume of the fermentation reactor of the second pair and the volume of the fermented broth contained in the fermentation reactor of the first pair in which the first preparatory fermentation of the methane-generating bacteria occurred. This operation can be performed for example by using a volumetric pump. The second "preparatory fermentation" occurs in the fermentation reactor of the second pair of the battery: once transfer has occurred, carbon dioxide is bubbled in the fermentation reactor with a flow that is proportional to the volume of the fermentation reactor. Preferably, this flow can be determined by multiplying the volume of the fermentation reactor by a coefficient the value of which is chosen as a function of the microorganisms that are present in the fermentation reactor and is comprised between 100 and 300 g/l/h (g/l per hour). Fermentation continues, appropriately controlling the temperature, the pH and the addition of nutrients and microelements, as it is known to the person skilled in the art, until the steady state of growth is reached. In the steady state, the fermentation reactor of the second pair dedicated to the growth of the methane-generating bacteria typically contains at least 3.5 billion cells/ml; a time comprised between 10 and 18 hours is usually necessary in order to reach this concentration.

Once the steady state has been reached, the entire content of the fermentation reactor of the second pair is transferred into the fermentation reactor of the third pair dedicated to the growth of the methane-generating bacteria, loaded beforehand with culture broth for a quantity equal to the difference between the effective volume of the fermentation reactor of the third pair and the volume of the fermented broth contained in the fermentation reactor of the second pair in which the second preparatory fermentation of the methane-generating bacteria occurred. Once transfer has occurred, carbon dioxide is bubbled in the fermentation reactor with a flow that is proportional to the volume of the fermentation reactor. Preferably, this flow can be determined by multiplying the volume of the fermentation reactor by a coefficient the value of which is chosen as a function of the microorganisms that are present in the fermentation reactor and is comprised between 100 and 300 g/l/h (g/l per hour). In order to allow methane production, the hydrogen produced by the cyanobacteria and/or microalgae is also bubbled in the fermentation reactor with a flow that is proportional to the volume of the fermentation reactor. Preferably, this flow can be determined by multiplying the volume of the fermentation reactor by a coefficient the value which is chosen as a function of the microorganisms that are present in the fermentation reactor and is comprised between 400 and 1200 g/l/h (g/l per hour). Fermentation continues, controlling appropriately the temperature, the pH and the addition of nutrients and microelements, as it is known to the person skilled in the art. The "process fermentation", in which both the absorption of carbon dioxide and the production of methane, generally produced with a flow comprised between 110 and 150 g/l/h (g/l per hour), are maximized and given continuity, occurs in the fermentation reactor of the third pair of the battery that is dedicated to the growth of the methane-generating bacteria; the methane is captured by means of an extractor (or other equivalent system) and sent to a gas storage system, from where it can be sent to energy conversion or introduced in the natural gas distribution network.

In order to maximize and give continuity both to the absorption of $CO_2$ and to the production of methane, once the steady state has been reached (in which, as stated, the concentration of microorganisms is typically equal to at least 3.5 billion cells/ml), it is possible to repeat in the process fermentation reactor a cycle that comprises additionally the steps of unloading approximately ⅓ of the volume of the fermented broth into a centrifuge provided with a decanter;

loading new culture broth for a volume equal to the volume of the unloaded fermented broth;

restarting the growth of the microorganisms, with bubbling of the carbon dioxide with a flow that is proportional to the volume of the fermentation reactor, until the steady state is reached again.

After the beginning of the process fermentation, the fermentation reactors of the first and second pairs dedicated to the growth of the methane-generating bacteria generally undergo sterilization, so that they can be reused if, due to anomalies in the process fermentation, it is necessary to renew the mass of microorganisms.

The fermented broth unloaded into the decanter centrifuge is separated by the latter into a semisolid component and a liquid component. The semisolid component amounts to approximately 35% by weight of the broth and consists of the biomass (i.e., the microorganisms) which, after sterilization, can be used for the production of humus. The liquid component amounts to approximately 65% by weight of the broth: by means of a purification process, it is possible to recover from the liquid component water to be reused for the preparation of the culture broths and to produce sludges, which also can be used to produce humus.

2. Symbiosis of the Second Kind

Sulfobacteria are capable of using the ammonium ($NH_4^+$) present in the culture broth as a source of nitrogen, producing $H_2$ and organic nitrogenous compounds by anoxygenic nitration. The growth of these bacteria is stimulated by the continuous removal of the hydrogen they produce, which is absorbed by the methane-generating bacteria, which use it in the synthesis of methane.

Acetobacteria are capable of producing organic compounds such as for example acetic acid, butyric acid, lactic acid, producing $H_2$ at the same time. In this case also, the absorption of the hydrogen by the methane-generating bacteria stimulates the growth of the acetobacteria.

As explained earlier, symbiosis of the second type can be performed advantageously in a single environment, since both the categories of microorganisms involved (sulfobacteria and/or acetobacteria and methane-generating bacteria) have the same requirements in nutritional terms (the need for organic substrates for cell growth) and in terms of culture conditions (strictly anaerobic environment, pH). Symbiosis of the second kind can be performed in one or more batteries; preferably, each battery consists of a certain number of fermentation reactors arranged in series and having increasing effective volumes. The number of batteries, the number of fermentation reactors of each battery and the effective volume of the fermentation reactors can be variable according to the quantities of carbon dioxide to be treated. Preferably, it is possible to use one or more batteries, each of which consists of five fermentation reactors: two pairs of preparatory fermentation reactors, arranged in series (in which sulfobacteria and/or acetobacteria and methane-generating bacteria are cultured separately) and a single process fermentation reactor, in which the two types of microorganism are reunited in the same environment in order to perform symbiosis. Furthermore, it is preferable that each pair of preparatory fermentation reactors of the battery has an effective volume that is at least twice the effective volume of the preceding pair of preparatory fermentation reactors. Likewise, it is preferable that the process fermentation reactor has an effective volume that is at least twice the total effective volume of the last pair of preparatory fermentation reactors.

In the following, for the sake of simplicity, methanation by symbiosis of the second type is described, with a single battery consisting of five fermentation reactors, two pairs of preparatory fermentation reactors, for the growth of each symbiont separately, as explained above, and a process fermentation reactor for providing the actual methanation; if multiple batteries are used, the same procedure is applied identically to each battery.

First of all, the culture broths for the growth of each symbiont are prepared by using a mixer for liquids for each broth, which has a volume equal to approximately 60% of the sum of the effective volumes of the entire fermentation battery; preferably, it is possible to use three mixers, one main mixer and two secondary mixers, wherein the main mixer has an effective volume that is equal at least to approximately 60% of the sum of the effective volumes of the entire fermentation battery and wherein each one of the two secondary mixers has an effective volume equal to approximately half of the effective volume of the main mixer. The culture broths are prepared on the basis of the selected microorganisms, following the specifications indicated by the ATCC and as it is known to the person skilled in the art. The typical composition of the culture broths for the various microorganisms is given in Annex A. Since the microorganisms involved in the symbiosis of the second kind live in a strictly anaerobic environment, the culture broth must be deprived of molecular oxygen, for example by means of a plenum and a vacuum pump, before they are poured into the fermentation reactors.

A seeding liquid for each symbiont, comprising the selected microorganism and the corresponding culture broth, is then prepared in an incubator (for example of the Dubnoff or equivalent type), typically by using a seeding flask with an effective volume equal to approximately $1/100$ of the effective volume of each fermentation reactor of the first pair of the battery.

The first "preparatory fermentation" occurs in the first pair of fermentation reactors of the battery: the sulfobacteria and/or acetobacteria are cultured in one fermentation reactor, and the methane-generating bacteria are cultured in the other fermentation reactor. The seeding liquid that contains the sulfobacterium and/or the acetobacterium and the seeding liquid that contains the methane-generating bacterium (or optionally the seeding liquids if multiple microorganisms are used) are each poured into one of the fermentation reactors of the first pair of the battery, together with additional culture broth, suitable for each microorganism, until the entire effective volume of the fermentation reactor is reached. Following the seeding, the bacterial mass in each fermentation reactor of the first pair is typically equal to approximately 10 million cells/ml. Once seeding has occurred, carbon dioxide is bubbled in both fermentation reactors of the first pair with a flow that is proportional to the volume of the fermentation reactors. Preferably, this flow can be determined by multiplying the volume of the fermentation reactor by a coefficient whose value is chosen as a function of the microorganisms that are present in the fermentation reactor and is comprised between 250 and 500 g/l/h (g/l per hour). Although, as stated, sulfobacteria and acetobacteria require organic substances more complex than carbon dioxide for their growth, $CO_2$ is still bubbled also in the fermentation reactors dedicated to the growth of these microorganisms, in order to keep the environment of the fermentation reactor anoxic (i.e., without molecular oxygen). Fermentation continues, appropriately controlling the temperature, the pH and the addition of nutrients and microelements, as it is known to the person skilled in the art, until the steady state of growth is reached. In the steady state, each fermentation reactor of the first pair typically contains at least 3.5 billion cells/ml; a time comprised between 24 and 56 hours is usually needed to reach this concentration.

Once the steady state has been reached, the entire content of the fermentation reactors of the first pair is transferred, separately, into the fermentation reactors that form the second pair, loaded beforehand with the culture broth suitable for each microorganism for a quantity equal to the difference between the effective volume of each fermentation reactor of the second pair and the volume of the fermented broth contained in each fermentation reactor of the first pair in which the first preparatory fermentation occurred. This operation can be performed for example by using a volumetric pump. The second "preparatory fermentation" occurs in the fermentation reactors of the second pair of the battery, in which the sulfobacteria and/or acetobacteria and the methane-generating bacteria are still cultured separately. Once transfer has occurred, carbon dioxide is bubbled in both the fermentation reactors of the second pair with a flow that is proportional to the volume of the fermentation reactors. Preferably, this flow can be determined by multiplying the volume of the fermentation reactor by a coefficient the value of which is chosen as a function of the microorganisms that are present in the fermentation reactor and is comprised between 250 and 500 g/l/h (g/l per hour). Fermentation continues, appropriately controlling the temperature, the pH and the addition of nutrients and microelements, as it is known to the person skilled in the art, until the steady state of growth is reached. In the steady state, each fermentation reactor of the second pair typically contains at least 3.5 billion cells/ml; a time comprised between 8 and 18 hours is usually required in order to reach this concentration.

Once the steady state has been reached, the entire content of the two fermentation reactors of the second pair is transferred into the third fermentation reactor, loaded beforehand with culture broth for a quantity equal to the difference between the effective volume of the third fermentation reactor and the total volume of the fermented broth contained in the two fermentation reactors of the second pair. In the third fermentation reactor, the sulfobacteria/acetobacteria and the methane-generating bacteria are joined in the same reaction environment and therefore the culture broth added in the third fermentation reactor must be a mixture of broth for the growth of the methane-generating bacteria and broth for the growth of the sulfobacteria and/or acetobacteria, where a percentage comprised between 30% and 50% by weight on the total weight of the mixture consists of the broth for the growth of the sulfobacteria and/or acetobacteria.

The presence of sulfobacteria and/or acetobacteria and of methane-generating bacteria in the same environment allows the symbiosis leading to the production of methane to start. Once the transfer has occurred, carbon dioxide is bubbled in the third fermentation reactor with a flow that is proportional to the volume of the fermentation reactor. Preferably, said flow can be determined by multiplying the volume of the fermentation reactor by a coefficient whose value is chosen as a function of the microorganisms that are present in the fermentation reactor and is comprised between 250 and 500 g/l/h (g/l per hour). Fermentation continues, appropriately controlling the temperature, the pH and the addition of nutrients and microelements, as it is known to the person skilled in the art. The "process fermentation", in which both the absorption of carbon dioxide and the production of methane are maximized and given continuity, occurs in the third fermentation reactor of the battery, said methane being generally produced with a flow comprised between 110 and 150 g/l/h (g/l per hour); the methane is captured by means of an extractor (or other equivalent system), sent to a gas storage system and subsequently used for the generation of energy or introduced in the natural gas distribution network.

In order to maximize and give continuity both to the absorption of $CO_2$ and to the production of methane, once the steady state (in which, as stated, the concentration of microorganisms is typically equal to at least 3.5 billion cells/ml) has been reached, it is possible to repeat in the process fermentation reactor a cycle further comprising the steps of:
unloading approximately ⅓ of the volume of the fermented broth into a centrifuge provided with a decanter;
loading new culture broth for a volume equal to the volume of the unloaded fermented broth;
restarting the growth of the microorganisms, with bubbling of the carbon dioxide with a flow that is proportional to the volume of the fermentation reactor, until the steady state is reached again.

After the beginning of the process fermentation, the fermentation reactors of the first and second pairs generally undergo sterilization, so that they can be reused if, due to anomalies in the process fermentation, it is necessary to renew the mass of microorganisms.

The fermented broth unloaded in the decanter centrifuge is separated by the latter into a semisolid component and a liquid component. The semisolid component amounts to approximately 25% by weight of the broth and consists of the biomass (i.e., the microorganisms) which, after sterilization, can be used for the production of humus or for the subsequent symbiotic cultures. The liquid component amounts to approximately 75% by weight of the broth: by means of a purification process, it is possible to recover from the liquid component water to be reused for the preparation of the culture broths and to produce sludges, which also can be used to produce humus or for subsequent symbiotic cultures.

Regardless of the type of symbiosis used, a preferred embodiment of the method according to the disclosure can comprise the provision of an additional step, in which the biomass involved in the symbiosis is used for the production of humus or humatic fertilizers. The biomass is represented by the set of the microorganisms that take part to the symbiosis. Preferably, spent culture broths, rich in organic substances produced by the microorganisms during their cell growth, also can be used to produce humus or humatic fertilizers. Various methods for the production of humus and humatic fertilizers starting from a biomass and/or organic material are known and commonly used in the background art. Preferably, it is possible to use the method for the production of humatic products described in Italian patent no. 01298306 in the name of Riccardo Reverso.

The production of humus or humatic fertilizers, typically provided at the end of the methanation process, offers the dual advantage of contributing to the elimination of process waste produced by methanation, i.e., the biomass itself and the organic residue, using them at the same time in the production of an item with high added value (humus, indeed) which is employed in the agricultural field as a natural fertilizer and/or for pedologic correction of soils.

Also regardless of the type of symbiosis used, another preferred embodiment of the method according to the disclosure can comprise a further step, performed before symbiosis and identified hereinafter as "biomass production step". In this step, one or more hetero-autotrophic cyanobacteria and one or one or more microalgae selected among the ones listed in Tables 2 and 3 are grown in order to increase the biomass.

In the biomass production step, the indicated microorganisms are cultured individually, since no symbiosis is required. The provision of the biomass production step upstream the process for methane production by metabolization of the carbon dioxide offers mainly two advantages. First of all, since the cyanobacteria and the microalgae are capable of absorbing carbon dioxide and using it as an energy source for their own growth, providing this step allows to dispose of larger quantities of this gas. Furthermore, cyanobacteria and microalgae, during their growth, produce organic material that is easy to assimilate and can be used both as a nutrient for the bacteria used in methanation which require carbon sources more complex than $CO_2$ (methane-generating bacteria, sulfobacteria, acetobacteria) and in the production of humus.

The biomass production step can be performed in one or more batteries; preferably, each battery consists of a certain number of fermentation reactors arranged in series and having increasing effective volumes. The number of batteries, the number of fermentation reactors of each battery, and the effective volume of the fermentation reactors can be variable depending on the quantities of carbon dioxide to be processed. Preferably, it is possible to use one or more batteries, each of which consists of three fermentation reactors. Furthermore, it is preferable that each fermentation reactor of the battery has an effective volume that is one order of magnitude greater than the effective volume of the preceding fermentation reactor.

Although the biomass production step can be performed by using a single microorganism among the ones that belong to the class of hetero-autotrophic cyanobacteria or of microalgae listed in Tables 2 and 3, the use of at least two microorganisms, of which at least one is a hetero-autotrophic cyanobacterium and at least one is a microalga, is preferable. Even more preferably, hetero-autotrophic cyanobacteria and microalgae can be used in a quantitative ratio of ⅕ hetero-autotrophic cyanobacteria and ⅘ microalgae. The use of at least one hetero-autotrophic cyanobacterium and at least one microalga in the biomass production step ensures better results, both in terms of carbon dioxide absorption and in terms of quality of the produced biomass: the organic compounds produced by the microalgae are in fact more suitable to favor the methanation reaction than the more complex proteins produced by the cyanobacteria.

In the following, for the sake of simplicity the step of biomass production with a single battery consisting of three fermentation reactors is described; if multiple batteries are used, the same procedure is applied identically to each battery.

First of all, the culture broth for the growth of the microorganism chosen for the production of biomass is prepared by using a mixer for liquids that has a volume equal to approximately 60% of the sum of the effective volumes of the entire fermentation battery; the culture broth is prepared according to the selected microorganism, following the specifications given by the ATCC and as it is known to the person skilled in the art. The typical composition of the culture broths for the various microorganisms is given in Annex A. If two or more microorganisms are used, the fermentation reactors must contain a mixture of culture broths suitable for the growth of all of the microorganisms used, in the same quantitative ratio as the microorganisms that are present.

Then, in an incubator (for example of the Dubnoff type or equivalent), a seeding liquid is prepared which comprises the selected microorganism and the corresponding culture broth, typically by using a seeding flask with an effective volume equal to approximately $1/100$ of the effective volume of the first fermentation reactor of the battery.

The first "preparatory fermentation" occurs in the first fermentation reactor of the battery: the seeding liquid that contains the microorganism is poured into the first fermentation reactor of the battery, together with additional culture broth, until the entire effective volume of the fermentation reactor is reached. Following the seeding, the quantity of microorganisms present in the first fermentation reactor is typically close to 10 million cells/ml. Once seeding has occurred, carbon dioxide is bubbled in the fermentation reactor with a flow that is proportional to the volume of the fermentation reactor. Preferably, this flow can be determined by multiplying the volume of the fermentation reactor by a coefficient the value of which is chosen as a function of the microorganisms that are present in the fermentation reactor and is comprised between 50 and 200 g/l/h. (g/l per hour), more preferably between 100 and 200 g/l/h. Fermentation continues, appropriately controlling the temperature, the pH and the addition of microelements, as it is known to the person skilled in the art, until the steady state of growth is reached. In the steady state, the first fermentation reactor typically contains at least 3.5 billion cells/ml; a time comprised between 24 and 56 hours is usually necessary to reach this concentration.

Once the steady state has been reached, the entire content of the first fermentation reactor is transferred into the second fermentation reactor, loaded beforehand with culture broth for a quantity equal to the difference between the effective volume of the second fermentation reactor and the volume of the fermented broth contained in the first fermentation reactor. This operation can be performed for example by using a volumetric pump. The second "preparatory fermentation" occurs in the second fermentation reactor of the battery: once the transfer has occurred, carbon dioxide is bubbled in the fermentation reactor with a flow that is proportional to the volume of the fermentation reactor. Preferably, this flow can be determined by multiplying the volume of the fermentation reactor by a coefficient the value of which is chosen as a function of the microorganisms that are present in the fermentation reactor and is comprised between 50 and 200 g/l/h (g/l per hour), more preferably between 100 and 200 g/l/h. Fermentation continues, appropriately controlling the temperature, the pH and the addition of microelements, as it is known to the person skilled in the art, until the steady state of growth is reached. In the steady state, the second fermentation reactor typically contains at least 3.5 billion cells/ml; a time comprised between 8 and 18 hours is usually required to reach this concentration.

Once the steady state has been reached, the entire content of the second fermentation reactor is transferred into the third fermentation reactor, loaded beforehand with culture broth for a quantity equal to the difference between the effective volume of the third fermentation reactor and the volume of the fermented broth contained in the second fermentation reactor. Once the transfer has occurred, carbon dioxide is bubbled in the fermentation reactor with a flow that is proportional to the volume of the fermentation reactor. Preferably, this flow can be determined by multiplying the volume of the fermentation reactor by a coefficient the value of which is chosen as a function of the microorganisms that are present in the fermentation reactor and is comprised between 50 and 200 g/l/h (g/l per hour), more preferably between 100 and 200 g/l/h. Fermentation continues, appropriately controlling the temperature, the pH and the addition of microelements, as it is known to the person skilled in the art. The "process fermentation", during which both absorption of carbon dioxide and biomass production are maximized and given continuity, occurs in the third fermentation reactor of the battery; for this purpose, once the steady state (in which, as stated, the concentration of microorganisms is typically equal to at least 3.5 billion cells/ml) is reached, it is possible to repeat in the process fermentation reactor a cycle further comprising the steps of unloading approximately $1/3$ of the volume of the fermented broth into a centrifuge provided with a decanter;

loading new culture broth for a volume equal to that of the unloaded fermented broth;

restarting the growth of microorganisms, with bubbling of the carbon dioxide with a flow that is proportional to the volume of the fermentation reactor, until the steady state is reached again.

After the beginning of the process fermentation, the first and second fermentation reactors generally undergo sterilization, so that they can be reused if, due to anomalies in the process fermentation, it is necessary to renew the mass of microorganisms.

The fermented broth unloaded into the decanter centrifuge is separated by the latter into a semisolid component and a liquid component. The semisolid component amounts to approximately 25% by weight of the broth and consists of the biomass (i.e., the microorganisms), which, after sterilization, can be used for methanation. The liquid component amounts to approximately 75% by weight of the broth: by means of a purification process, it is possible to recover from the liquid component water to be reused for the preparation of the culture broths and to produce sludges, which also can be used to produce humus.

If the microorganisms used are microalgae, in order to complete the photosynthesis with the step of carbon fixation (also known as "dark step" or "Calvin cycle"), it is possible to use the lamps with which fermentation reactors are equipped for a period comprised between 12 and 20 hours/day.

In practice it has been found that the method for the production of methane by biological conversion of carbon dioxide performed by symbiosis as described herein achieves fully the intended aim and advantages, since it allows to obtain methane with a high degree of purity and with good yields. The method according to the disclosure also allows to dispose of the carbon dioxide contained in gaseous emissions, which is first absorbed and converted into methane by the methane-generating bacteria and, if a symbiosis of the first kind, is performed, it is used as a source of carbon by cyanobacteria and microalgae. Moreover, the method according to the disclosure allows to obtain organic material that is easy to assimilate and can be used as a raw material in subsequent symbioses in series (which amplify the method itself, further increasing methane yields) or in the production of humus.

The method for biological conversion of carbon dioxide to methane (methanation) conceived as described herein is susceptible of numerous modifications and variations, all of which are within the scope of the inventive concept; all the details may furthermore be replaced by other elements the equivalence of which is known to the person skilled in the art.

The disclosures in Italian Patent Application No. 102015000073679 (UB2015A005703) from which this application claims priority are incorporated herein by reference.

Annex A

Culture Broths for Growing Hetero-Autotrophic Cyanobacteria

| Strain | Broth formulation | | pH | Temperature (° C.) |
|---|---|---|---|---|
| *Sporotomaculatum hydroxybenzoicum* (ATCC no. 700645) | $KH_2PO_4$ | 0.2 g | 7.6 | 30 |
| | $NH_4Cl$ | 0.3 g | | |
| | KCl | 0.5 g | | |
| | NaCl | 1.0 g | | |
| | $CaCl_2 \cdot 2H_2O$ | 0.5 g | | |
| | $MgCl_2 \cdot H_2O$ | 0.4 g | | |
| | Hcl (25%) | 10 ml | | |
| | $FeCl_2 \cdot 4H_2O$ | 1 5 g | | |
| | $ZnCl_2$ | 70.0 mg | | |
| | $MnCl_2 \cdot 4H_2O$ | 100 mg | | |
| | $H_3BO_3$ | 6 mg | | |
| | $CoCl_2 \cdot 6H_2O$ | 190 mg | | |
| | $CuCl_2 \cdot 2H_2O$ | 2 g | | |
| | $NiCl_2 \cdot 6H_2O$ | 24 mg | | |
| | $Na_2MoO_4 \cdot 2H_2O$ | 36 mg | | |
| | Distilled water | 990 ml | | |
| *Formivibrio citricus* (ATCC no. 42791) | Sodium hydrate | 2.94 g | 7.7 | 30 |
| | $NH_4Cl$ | 0.53 g | | |
| | $KH_2PO_4$ | 1.36 g | | |
| | $Cl_2 \cdot 6H_2O$ | 2.03 g | | |
| | $CaCl_2 \cdot 2H_2O$ | 0.15 g | | |
| | $Na_2SeO_3$ | 1 mg | | |
| | $NiCl_2 \cdot 6H2O$ | 1 mg | | |
| | $Na_2WO_4 \cdot 2O$ | 1 mg | | |
| | Nitrilotriacetic acid | 1.5 mg | | |
| | $MgSO_4 \cdot 7H_2O$ | 3 mg | | |
| | $MnSO_4 \cdot H_2O$ | 0.5 mg | | |
| | NaCl | 1 mg | | |
| | $FeSO_4 \cdot 7H_2O$ | 0.1 mg | | |
| | $CoCl_2 \cdot 6H_2O$ | 0.1 mg | | |
| | $CaCl_2$ | 0.1 mg | | |
| | $ZnSO_4 \cdot 7H_2O$ | 0.1 mg | | |
| | $CuSO_4 \cdot 5H_2O$ | 0.01 mg | | |
| | $AlK(SO_4)_2 \cdot 2H_2O$ | 0.01 mg | | |
| | Distilled water | 1 lt | | |
| *Rhodococcus rhodochrous* (ATCC no. 21198) | Yeast extract | 10 g | 7.0 | 26 |
| | Maltose | 2 g | | |
| | Distilled water | 1 lt | | |
| *Moorella thermoacetica* (ATCC no. 39073) | $KH_2PO_4$ | 1.5 g | 7.0 | 55 |
| | $K_2HPO_4$ | 2.9 g | | |
| | Sodium thioglycolate | 0.5 g | | |
| | Resazurin (1.0% solution) | 2 ml | | |
| | $(NH_4)2SO_4$ | 1.3 g | | |
| | $MgCl_2$ | 0.75 g | | |
| | NaCl | 1 g | | |
| | $CaCl_2$ | 13.2 mg | | |
| | $FeSO_4$ (1.25% solution) | 0.1 ml | | |
| | Cellobiose | 6 g | | |
| | Yeast extract | 5.0 g | | |
| | Distilled water | 1 lt | | |
| *Moorella thermoacetica* (ATCC no. 49073) | $KH_2PO_4$ | 1.5 g | 7.0 | 55 |
| | $K_2HPO_4$ | 2.9 g | | |
| | Sodium thioglycolate | 0.5 g | | |
| | Resazurin (1.0% solution) | 2 ml | | |
| | $(NH_4)2SO_4$ | 1.3 g | | |
| | $MgCl_2$ | 0.75 g | | |
| | NaCl | 1 g | | |
| | $CaCl_2$ | 13.2 mg | | |
| | $FeSO_4$ (1.25% solution) | 0.1 ml | | |
| | Cellobiose | 6 g | | |
| | Yeast extract | 5.0 g | | |
| | Distilled water | 2 lt | | |
| | Agar | 20 g | | |
| | (broth to be prepared in an environment saturated with 97% nitrogen and 3% hydrogen) | | | |
| *Lactobacillus helveticus* (ATCC no. 55163) | Lactobacillus MRS Broth DIFCO | 22 g | 7.0 | 37 |
| *Cochilliobus cynodontis* (ATCC no. 24938) | Sodium nitrate | 3 g | 7.0 | 24 |
| | Dipotassium sulfate | 1 g | | |
| | Magnesium sulfate | 0.5 g | | |
| | Potassium chloride | 0.5 g | | |
| | Ferrous sulfate | 0.01 g | | |
| | Agar | 15 g | | |
| | Distilled water | 900 ml | | |
| | Sugar (30% solution in water) | 1 lt | | |
| *Camorosporium robinae* (ATCC no. 16673) | Yeast extract | 3 g | 6.2 | 35 |
| | Malt extract | 3 g | | |
| | Dextrose | 10 g | | |
| | Peptone | 5 g | | |
| | Agar | 20 g | | |
| | Distilled water | 1 lt | | |
| *Acetomicrobium flavidum* (ATCC no. 43122) | $K_2HPO_4 \cdot 3H_2O$ | 0.4 g | 7.9 | 35 |
| | $NH_4Cl$ | 1 g | | |
| | NaCl | 0.45 g | | |
| | Yeast extract | 2 g | | |
| | L-cysteine chloride | 0.15 g | | |
| | Saline solution[(1)] | 10 ml | | |
| | [(1)]Saline solution: | | | |
| | $H_2SeO_3$ | 0.01 g | | |
| | $MnCl_2 \cdot 4H_2O$ | 0.10 g | | |
| | $FeSO_4 \cdot 7H_2O$ | 0.10 g | | |
| | $CoCl_2 \cdot 6H_2O$ | 0.15 g | | |
| | $ZnCl_2$ | 0.10 g | | |
| | $H_3BO_3$ | 0.01 g | | |
| | $Na_2MoO_4 \cdot 2H_2O$ | 0.01 g | | |
| | $CuCl_2 \cdot 2H_2O$ | 0.02 g | | |
| | $NiSO_4 \cdot 6H_2O$ | 0.02 g | | |
| | $AlCl_3 \cdot 6H_2O$ | 0.04 g | | |
| | EDTA | 0.50 g | | |
| | Distilled water | 1 lt | | |

Culture Broths for Growing Microalgae

| Strain | Broth formulation | | pH | Temperature (° C.) | Light |
|---|---|---|---|---|---|
| *Chlorella vulgaris* (ATCC no. 30581; 13482; 30821; 9765) | Saline solution[(1)] | 10 ml | 6.8 | 26 | 450 nm |
| | $FeCl_3$ | 1 g | | | |
| | Peptone | 1 g | | | |
| | $H_2O$ | 1 lt | | | |
| | [(1)]Saline solution | | | | |
| | $NaNo_3$ | 10 g | | | |
| | $CaCl_2$ | 1 g | | | |
| | $MgSO_4 \cdot 7H_2$ | 3 g | | | |
| | $K_2HPO_4$ | 3 g | | | |
| | $KH_2PO_4$ | 7 g | | | |

| Strain | Broth formulation | | pH | Temperature (° C.) | Light |
|---|---|---|---|---|---|
| | NaCl | 1 g | | | |
| | H$_2$O | 400 ml | | | |
| Chlorella vulgaris Beijerinck (ATCC no. 11468) | Same broth formulation, pH and temperature as "Chlorella vulgaris" | | | | 450 nm |
| Chlorella vulgaris var. viridis (ATCC no. 16487) | Same broth formulation, pH and temperature as "Chlorella vulgaris" | | | | 450 nm |
| Chlorella pyrenoidosa (ATCC no. 30582) | Same broth formulation as "Chlorella vulgaris" | | 7.0 | 30 | 450 nm |
| Euglena gracilis var. bacillaris (ATCC no. 10616) | KH$_2$PO$_4$ | 0.02 g | 7.2 | 26 | — |
| | Potassium citrate | 0.04 g | | | |
| | Magnesium sulfate | 0.02 g | | | |
| | Peptone | 0.6 g | | | |
| | Thiamine | 0.04 mg | | | |
| | Vitamin B$_{12}$ | 0.05 mcg | | | |
| | Yeast extract | 0.04 g | | | |
| | Distilled water | 1 lt | | | |
| Euglena gracilis var. saccharophila (ATCC no. 12893) | Same broth formulation, pH and temperature as "Euglena gracilis var. bacillaris" | | | | |
| Euglena gracilis (ATCC no. 12716) | Same broth formulation, pH and temperature as "Euglena gracilis var. bacillaris" | | | | |
| Scenedesmus obliquus (ATCC no. 11477) | Yeast extract | 1 g | 7.5 | 30 | — |
| | Meat extract | 1 g | | | |
| | Tryptose | 2 g | | | |
| | Ferrous sulfate | 0.002 g | | | |
| | Dextrose | 10 g | | | |
| | Distilled water | 1 lt | | | |
| Pleurochloris commutata (ATCC no. 11474) | Same broth formulation and temperature as "Scendesmus obliquus" | | | | |
| Anabaena sp. (ATCC no. 27899) | NaNO$_3$ | 1.5 g | 7.1 | 26 | 3 lux |
| | K$_2$HPO$_4$ | 0.04 g | | | |
| | MgSO$_4$•7H$_2$O | 0.075 g | | | |
| | CaCl$_2$•2H$_2$O | 0.036 g | | | |
| | Citric acid | 6 mg | | | |
| | Ferric ammonium citrate | 6 mg | | | |
| | EDTA | 1 mg | | | |
| | Na$_2$CO$_3$ | 0.02 g | | | |
| | Mixture of metals[1] | 1 ml | | | |
| | Mixture of 80% seawater-20% mains water | 1 lt | | | |
| | [1]Mixture of metals | | | | |
| | H$_3$BO$_3$ | 2.86 g | | | |
| | MnCl$_2$•4H$_2$O | 1.81 g | | | |
| | ZnSO$_4$•7H2O | 0.222 g | | | |
| | Na$_2$MoO$_4$ | 0.39 g | | | |
| | CuSO$_4$•5H$_2$O | 0.079 g | | | |
| | Co(NO$_3$)$_2$•H$_2$O | 49.4 mg | | | |
| | Mixture of 80% seawater-20% mains water | 1 lt | | | |

Culture Broths for Growing Methane-Generating Bacteria

| Strain | Broth formulation | | pH | Temperature (° C.) |
|---|---|---|---|---|
| Methanothermobacter thermoautotrophicus (ATCC no. 29096) | Sodium bicarbonate | 8.4 g | 7.0-7.3 | 35 |
| | Distilled water | 976 ml | | |
| | Solution A[1] | 10 ml | | |
| | Solution B[2] | 2 ml | | |
| | Yeast extract | 2 g | | |
| | Peptone | 2 g | | |
| | Solution C[3] | 2 ml | | |
| | (broth to be prepared in an environment saturated with 70% nitrogen and 30% carbon dioxide) | | | |
| | [1]Solution A | | | |

-continued

| Strain | Broth formulation | | pH | Temperature (° C.) |
|---|---|---|---|---|
| | Ammonium chloride | 100 g | | |
| | Magnesium chloride | 100 g | | |
| | Calcium chloride | 40 g | | |
| | Distilled water | 1 lt | | |
| | (2)Solution B | | | |
| | Dipotassium phosphate | 200 g | | |
| | Distilled water | 1 lt | | |
| | (3)Solution C | | | |
| | Resazurin | 0.5 g | | |
| | Distilled water | 1 lt | | |
| *Methanosarcina barkeri* Schnellen (ATCC no. 43569) | Same broth formulation, pH and temperature as "*Methanothermobacter thermoautotrophicus*" | | | |
| *Methanospirillum hungatei* (ATCC no. 27890) | Same broth formulation, pH and temperature as "*Methanothermobacter thermoautotrophicus*" | | | |
| *Methanococcus deltae* (ATCC no. 35294) | Saline solution(1) | 200 ml | 7.0 | 37 |
| | Solution of vitamins(2) | 4 ml | | |
| | 20% aqueous solution of yeast extract | 4 ml | | |
| | Resazurin 0.1% | 0.4 ml | | |
| | 25% sodium acetate solution | 2 ml | | |
| | 0.2% Fe(NH$_4$)2SO$_4$ solution | 0.4 ml | | |
| | NaHCO$_3$ | 2 g | | |
| | NaCl | 3.6 g | | |
| | Cysteine sulfite reducing agent | 16 ml | | |
| | (1)Saline solution | | | |
| | KCl | 0.67 g | | |
| | MgCl$_2$•6H$_2$O | 5.5 g | | |
| | MgSO$_4$•7H$_2$O | 6.9 g | | |
| | NH$_4$Cl | 0.5 g | | |
| | CaCl$_2$•2H$_2$O | 0.28 g | | |
| | K$_2$HPO$_4$ | 0.28 g | | |
| | Mains water | 1 lt | | |
| | (2)Solution of vitamins | | | |
| | Biotin | 2 mg | | |
| | Folic acid | 2 mg | | |
| | Hydrochloric pyridoxine | 10 mg | | |
| | Riboflavin | 5 mg | | |
| | Nicotinic acid | 5 mg | | |
| | Calcium D-(+)-pantothenate | 5 mg | | |
| | Vitamin B$_{12}$ | 0.1 mg | | |
| | p-aminobenzoic acid | 5 mg | | |
| | Thiocyanic acid | 5 mg | | |
| | Mains water | 1 lt | | |
| *Methanococcus vannielii* ATCC no. 35089 | Saline solution(1) | 200 ml | 7.2 | 35 |
| | Solution of vitamins(2) | 4 ml | | |
| | 20% yeast extract solution | 4 ml | | |
| | 20% sodium acetate solution | 2 ml | | |
| | 0.2% iron diammonium sulfate solution | 0.4 ml | | |
| | NaHCO$_3$ | 2 g | | |
| | NaCl | 3.6 g | | |
| | Distilled water | 180 ml | | |
| | (1)Saline solution | | | |
| | MgCl$_2$•6H$_2$O | 5.5 g | | |
| | MgSO$_4$•7H$_2$O | 6.9 g | | |
| | NH$_4$Cl | 0.5 g | | |
| | CaCl$_2$•2H$_2$O | 0.28 g | | |
| | K$_2$HPO$_4$ | 0.28 g | | |
| | Distilled water | 1 lt | | |
| | (2)Solution of vitamins | | | |
| | Biotin | 2 mg | | |
| | Folic acid | 2 mg | | |
| | Hydrochloric pyridoxine | 10 mg | | |
| | Thiamine chloride | 5 mg | | |
| | Riboflavin | 5 mg | | |
| | Nicotinic acid | 5 mg | | |
| | Calcium pantothenate | 5 mg | | |
| | Vitamin B12 | 0.1 mg | | |
| | p-aminobenzoic acid | 5 mg | | |
| | Distilled water | 1 lt | | |

-continued

| Strain | Broth formulation | | pH | Temperature (° C.) |
|---|---|---|---|---|
| *Methanococcoides methylutens* (ATCC no. 33938) | Sodium chloride | 23.4 g | 7.2 | 35 |
| | Magnesium sulfate | 6.3 g | | |
| | Yeast extract | 1 g | | |
| | Sodium carbonate | 5 g | | |
| | Ammonium chloride | 1 g | | |
| | Potassium chloride | 0.8 g | | |
| | Calcium chloride | 0.14 g | | |
| | Disodium phosphate | 0.6 g | | |
| | Resazurin | 1 mg | | |
| | Cysteine chloride | 0.25 g | | |
| | Sodium sulfide | 0.25 g | | |
| | Trimethylamine | 3 g | | |
| | Solution of minerals[1] | 10 ml | | |
| | Distilled water | 990 ml | | |
| | [1]Solution of minerals | | | |
| | Nitrilacetic acid | 2.5 g | | |
| | Magnesium sulfate | 3 g | | |
| | Sodium chloride | 1 g | | |
| | Ferrous sulfate | 0.1 g | | |
| | Calcium chloride | 1 g | | |
| | Cobalt chloride | 0.1 g | | |
| | Zinc sulfate | 0.1 g | | |
| | Copper sulfate | 0.01 g | | |
| | Aluminum potassium sulfate | 0.01 g | | |
| | Boric acid | 0.01 g | | |
| | Sodium molybdate | 0.01 g | | |
| | Distilled water | 1 lt | 7 | 38 |
| *Methanococcus maripaludis* (ATCC no. 43000) | Sodium chloride | 18 g | | |
| | Magnesium chloride | 2.75 g | | |
| | Potassium chloride | 0.335 g | | |
| | Magnesium sulfate | 3.45 g | | |
| | Ammonium chloride | 0.25 g | | |
| | Calcium chloride | 0.14 g | | |
| | Dipotassium phosphate | 0.14 g | | |
| | Element traces[1] | 10 ml | | |
| | Vitamin solutions[2] | 10 ml | | |
| | Iron ammonium sulfate | 2 mg | | |
| | Sodium bicarbonate | 5 g | | |
| | Sodium acetate | 1 g | | |
| | Yeast extract | 2 g | | |
| | Trypticase | 2 g | | |
| | Resazurin | 1 mg | | |
| | Cysteine chloride | 0.5 g | | |
| | Sodium sulfide | 0.5 g | | |
| | Distilled water | 1 lt | | |
| | (broth to be prepared in an environment saturated with 80% nitrogen and 20% carbon dioxide) | | | |
| | [1]Element traces | | | |
| | Zinc sulfate | 0.1 g | | |
| | Magnesium chloride | 0.03 g | | |
| | Boric acid | 0.3 g | | |
| | Cobalt chloride | 0.2 g | | |
| | Copper chloride | 0.01 g | | |
| | Nickel chloride | 0.02 g | | |
| | Sodium molybdate | 0.03 g | | |
| | Distilled water | 1 lt | | |
| | [2]Vitamin solution | | | |
| | Biotin | 2 mg | | |
| | Folic acid | 2 mg | | |
| | Pyridoxine chloride | 10 mg | | |
| | Thiamine chloride | 5 mg | | |
| | Riboflavin | 5 mg | | |
| | Nicotinic acid | 5 mg | | |
| | Calcium pantothenate | 5 mg | | |
| | Vitamin B12 | 0.01 mg | | |
| | p-aminobenzoic acid | 5 mg | | |
| | Thiolic acid | 1 mg | | |
| | Distilled water | 1 lt | | |
| *Methanococcus jannaschii* (ATCC no. 43067D-43067D-5) | Same broth formulation, pH and temperature as "*Methanococcus maripaludis*" | | | |

-continued

| Strain | Broth formulation | | pH | Temperature (° C.) |
|---|---|---|---|---|
| Methanobrevibacter arboriphilus (ATCC no. BAA-1958) | Same broth formulation, pH and temperature as "Methanococcus maripaludis" | | | |
| Methanosarcina mazei (Barker) Mah and Kuhn (ATCC no. BAA-159) | Same broth formulation, pH and temperature as "Methanococcus maripaludis" | | | |
| Methanococcus aeolicus (ATCC no. BAA-1280) | Same broth formulation, pH and temperature as "Methanococcus maripaludis" | | | |
| Methylococcus capsulatus (ATCC no. 33009) | Meat broth[1] | 1 lt | 7 | 33 |
| | Peptone | 30 g | | |
| | Yeast extract | 5 g | | |
| | Dipotassium phosphate | 5 g | | |
| | Resazurin sol. 25% | 4 ml | | |
| | Agar | 20 g | | |
| | l-cysteine chloride | 0.5 g | | |
| | Solution of hemin[2] | 10 ml | | |
| | Solution of vitamins[3] | 0.2 ml | | |
| | (broth to be prepared in environment saturated with 80% nitrogen, 10% hydrogen and 10% carbon dioxide) | | | |
| | [1]Meat broth | | | |
| | Beef | 500 g | | |
| | Distilled water | 1 lt | | |
| | Sodium hydrate solution 1 N | 25 ml | | |
| | filter and restore to volume of 1 lt with distilled water. | | | |
| | [2]Solution of hemin | | | |
| | Hemin atcc | 50 mg | | |
| | Sodium hydrate 1 N | 1 ml | | |
| | Distilled water | 100 ml | | |
| | [3]Solution of vitamins | | | |
| | Vitamin K1 | 0.15 ml | | |
| | Ethanol 95% | 30 ml | | |

Culture Broths for Growing Sulfobacteria and Acetobacteria

| Strain | Broth formulation | | pH | Temperature (° C.) | Light |
|---|---|---|---|---|---|
| Rhodobacter sphaeroides (ATCC no. 49419; 55304) | $K_2HPO_4$ | 1 g | 7.2 | 26 | 3 lux |
| | $MgSO_4$ | 0.5 g | | | |
| | Yeast extract | 10 g | | | |
| | Mains water | 1 lt | | | |
| Bacillus coagulans (ATCC no. 10545) | Meat extract | 5 g | 7.0 | 37 | — |
| | Yeast extract | 5 g | | | |
| Aceto-anaerobium noterae (ATCC no, 35199) | $K_2HPO_4 \cdot 3H_2O$ | 0.4 g | 7.9 | 35 | — |
| | $NH_4Cl$ | 1 g | | | |
| | NaCl | 0.45 g | | | |
| | Yeast extract | 2 g | | | |
| | L-cysteine chloride | 0.15 g | | | |
| | Saline solution[1] | 10 ml | | | |
| | 1) Saline solution | | | | |
| | $H_2SeO_3$ | 0.01 g | | | |
| | $MnCl_2 \cdot 4H_2O$ | 0.10 g | | | |
| | $FeSO_4 \cdot 7H_2O$ | 0.10 g | | | |
| | $CoCl_2 \cdot 6H_2O$ | 0.15 g | | | |
| | $ZnCl_2$ | 0.10 g | | | |
| | $H_3BO_3$ | 0.01 g | | | |
| | $Na_2MoO_4 \cdot 2H_2O$ | 0.01 g | | | |
| | $CuCl_2 \cdot 2H_2O$ | 0.02 g | | | |
| | $NiSO_4 \cdot 6H_2O$ | 0.02 g | | | |
| | $AlCl_3 \cdot 6H_2O$ | 0.04 g | | | |
| | EDTA | 0.50 g | | | |
| | Distilled water | 1 lt | | | |
| Rhodovolum sulphidofilum (ATCC no. 35886) | NaCl | 30 g | 7.0 | 37 | 3 lux |
| | Saline solution[1] | 1 ml | | | |
| | Solution of vitamins[2] | 1 ml | | | |
| | $KH_2PO_4$ | 1 g | | | |

-continued

| Strain | Broth formulation | | pH | Temperature (° C.) | Light |
|---|---|---|---|---|---|
| | $MgCl_2 \cdot 6H_2O$ | 0.5 g | | | |
| | $CaCl_2 \cdot 2H_2O$ | 0.1 g | | | |
| | $NH_4Cl$ | 1 g | | | |
| | $NaHCO_3$ | 3 g | | | |
| | $Na_2SO_4$ | 0.7 g | | | |
| | Sodium acetate | 1 g | | | |
| | Sodium ascorbate | 0.5 g | | | |
| | Yeast extract | 0.1 g | | | |
| | Distilled water | 1 lt | | | |
| | [1] Saline solution | | | | |
| | $CoCl_2 \cdot 6H_2O$ | 250 mg | | | |
| | $NiCl_2 \cdot 6H_2O$ | 10 mg | | | |
| | $CuCl_2 \cdot 2H_2O$ | 10 mg | | | |
| | $MnCl_2 \cdot 4H_2O$ | 70 mg | | | |
| | $ZnCl_2$ | 100 mg | | | |
| | $H_3BO_3$ | 500 mg | | | |
| | $Na_2MoO_4 \cdot 2H_2O$ | 30 mg | | | |
| | $Na_2SeO_3 \cdot 5H_2O$ | 10 mg | | | |
| | $FeCl_2 \cdot 4H_2O$ | 1.8 g | | | |
| | Distilled water | 1 lt | | | |
| | [2]Solution of vitamins | | | | |
| | Biotin | 50 mg | | | |
| | Nicotinamide | 175 mg | | | |
| | Thiamine chloride | 150 mg | | | |
| | p-aminobenzoic acid | 100 mg | | | |
| | Calcium pyridoxine | 50 mg | | | |
| | Cyanocobalamin chloride | 50 mg | | | |
| | Pantothenate | 25 mg | | | |
| | Distilled water | 500 ml | | | |

-continued

| Strain | Broth formulation | | pH | Temperature (° C.) | Light |
|---|---|---|---|---|---|
| Bacillus smithii (ATCC no. 55404) | Yeast extract | 1 g | 6.6 | 35 | — |
| | Tryptone | 1 g | | | |
| | Calcium chloride | 0.06 g | | | |
| | Sodium bicarbonate | 2 g | | | |
| | Solution C$^{(1)}$ | 80 ml | | | |
| | Solution of vitamins$^{(2)}$ | 50 ml | | | |
| | Mineral salts$^{(3)}$ | 3 mg | | | |
| | Glucose | 2 g | | | |
| | Distilled water | 920 ml | | | |
| $^{(1)}$Solution C | | | | | |
| | Monopotassium phosphate | 3 g | | | |
| | Dipotassium phosphate | 3 g | | | |
| | Ammonium sulfate | 6 g | | | |
| | Sodium chloride | 6 g | | | |
| | Magnesium sulfate | 1.25 g | | | |
| | Distilled water | 1 lt | | | |
| $^{(2)}$Solution of vitamins | | | | | |
| | Biotin | 2 mg | | | |
| | Folic acid | 2 mg | | | |
| | Pyridoxine hydrochloride | 10 mg | | | |
| | Thiamine chloride | 5 mg | | | |
| | Riboflavin | 5 mg | | | |
| | Nicotinic acid | 5 mg | | | |
| | Calcium pantothenate | 5 mg | | | |
| | Vitamin B12 | 0.1 mg | | | |
| | p-aminobenzoic acid | 5 mg | | | |
| | Thiolic acid | 5 mg | | | |
| | Distilled water | 1 lt | | | |
| $^{(3)}$Mineral salts | | | | | |
| | Mineral solution ATCC catalog no. MD-TMS | | | | |

Culture Broths for Growing Yeasts

| Strain | Broth formulation | | pH | Temperature (° C.) |
|---|---|---|---|---|
| Saccharomyces cerevisiae (ATCC no. 9896; 4024938) | Yeast extract | 3 g | 6.2 | 35 |
| | Malt extract | 3 g | | |
| | Dextrose | 10 g | | |
| | Peptone | 5 g | | |
| | Agar | 20 g | | |
| | Distilled water | 1 lt | | |
| Zygosaccharomyces florentius (ATCC no. 200584) | Same broth formulation, pH and temperature as "Saccharomyces cerevisiae" | | | |

The invention claimed is:

1. A method for producing methane by biological conversion of carbon dioxide, performed by means of a symbiosis between a first microorganism and a second microorganism, wherein:

said first microorganism is one or more bacteria selected from the group consisting of: Methanothermobacter thermoautotrophicus (ATCC No. 29096), Methanococcus deltae (ATCC No. 35294), Methanococcus vannielii (ATCC No. 35089), Methanococcoides methylutens (ATCC No. 33938), Methanocaldococcus jannaschii (ATCC No. 43067), Methanococcus maripaludis (ATCC No. 43000), Methanosarcina barkeri Schnellen (ATCC No. 43569), Methanospirillum hungatei (ATCC No. 27890), Methylococcus capsulatus (ATCC No. 33009), Methanosarcina mazei (Barker) Mah and Kuhn (ATCC No. BAA-159), and Methanococcus aeolicus (ATCC No. BAA 1280) and said second microorganism is:

(a) one or more microorganisms selected from the group consisting of: Anaerobaculum mobile (ATCC No. 43122), Rhodococcus rhodochrous (ATCC No. 21198), Moorella thermoacetica (ATCC No. 39073), Lactobacillus helveticus (ATCC No. 55163), Chlorella vulgaris Beijerinck (ATCC No. 11468), Chlorella vulgaris var. viridis (ATCC No. 16487), Chlorella sp. (ATCC No. 30582), Euglena gracilis (ATCC No. 12716), Euglena gracilis var. bacillaris (ATCC No. 10616), Euglena gracilis var. saccharophila (ATCC No. 12893), Scenedesmus obliquus (ATCC No. 11477), and Anabaena sp. (ATCC No. 27899)

or (b) one or more microorganisms selected from the group consisting of Rhodobacter sphaeroides (ATCC No. 49419), Rubrivivax sp. (ATCC No. 55304), Bacillus coagulans (ATCC No. 10545), Acetoanaerobium noterae (ATCC No. 35199), Rhodovulum sulfidophilum (ATCC No. 35886), and Bacillus smithii (ATCC No. 55404);

wherein:
if said second microorganism is one or more microorganism listed in (a), said first microorganism and said second microorganism are cultured in distinct and mutually connected fermentation reactors;
if said second microorganism is one or more microorganisms listed in (b), said first microorganism and said second microorganism are cultured in the same fermentation reactor;

comprising the steps of:
(i) providing a symbiotic culture, growing said first and second microorganisms until a steady state is reached, bubbling carbon dioxide in each fermentation reactor with a flow that is proportional to the volume of said fermentation reactor, so as to obtain the production of methane by the first microorganism; and
(ii) capturing and sending to storage the methane produced in step (i).

2. The method according to claim 1, wherein, upon reaching the steady state of growth of said first and second microorganisms the following additional steps are performed:
(iii) discharging from each fermentation reactor approximately ⅓ of the volume of the fermented broth into a centrifuge provided with a decanter;
(iv) loading into each fermentation reactor new culture broth for a volume equal to the volume of the discharged fermented broth;
(v) restarting the growth of the symbiotic culture until the steady state is reached, bubbling carbon dioxide in each fermentation reactor with a flow that is proportional to the volume of said fermentation reactor, so as to obtain the production of methane by the first microorganism; and
(vi) capturing and sending to storage the methane produced in step (v).

3. The method according to claim 1, wherein said second microorganism is one or more hetero-autotrophic cyanobacteria and/or microalgae.

4. The method according to claim 1, wherein said symbiotic culture is provided by means of multiple symbiotic cultures in series.

5. The method according to claim 4, wherein said multiple symbiotic cultures in series are in a number comprised between three and five.

6. The method according to claim 4, wherein said symbiotic cultures in series are provided in fermentation reactors, each of which has a larger effective volume than the preceding fermentation reactor.

7. The method according to claim 1, wherein if said second microorganism is one or more hetero-autotrophic cyanobacteria and/or microalgae, the flow of carbon dioxide in each fermentation reactor for the growth of said first microorganism is comprised between 100 and 300 g/l/h and the flow of carbon dioxide in each fermentation reactor for the growth of said second microorganism is comprised between 50 and 200 g/l/h.

8. The method according to claim 1, wherein, if said second microorganism is one or more sulfobacteria and/or acetobacteria, the flow of carbon dioxide in each fermentation reactor is comprised between 250 and 500 g/l/h.

9. The method according to claim 1, further comprising using the biomass consisting of said first microorganism and said second microorganism and/or the culture broths of said first microorganism and said second microorganism in the production of humus or humatic fertilizers.

10. The method according to claim 1, further comprising the growth of the biomass consisting of the second microorganism, wherein said second microorganism is one or more hetero-autotrophic cyanobacteria and/or microalgae, and wherein said growth is performed before said symbiosis by providing a culture of said second microorganism until the steady state is reached, bubbling carbon dioxide in each fermentation reactor with a flow that is proportional to the volume of said fermentation reactor.

11. The method according to claim 10, wherein, upon reaching the steady state of growth of said second microorganism, the following additional steps are performed:
(i) discharging from each fermentation reactor approximately ⅓ of the volume of the fermented broth into a centrifuge provided with a decanter;
(ii) loading into each fermentation reactor new culture broth for a volume equal to that of the discharged fermented broth; and
(iii) restarting the growth of the culture until the steady state is reached, bubbling carbon dioxide in each fermentation reactor with a flow that is proportional to the volume of said fermentation reactor.

12. The method according to claim 10, wherein said second microorganism is one or more hetero-autotrophic cyanobacteria and one or more microalgae.

13. The method according to claim 12, wherein said one or more hetero-autotrophic cyanobacteria and said one or more microalgae are in a quantitative ratio equal to ⅕ hetero-autotrophic cyanobacteria and ⅘ microalgae.

14. The method according to claim 10, wherein the flow of carbon dioxide in each fermentation reactor is comprised between 50 and 200 g/l/h.

* * * * *